United States Patent
Simanzhenkov et al.

(10) Patent No.: US 11,338,274 B2
(45) Date of Patent: *May 24, 2022

(54) OXIDATIVE DEHYDROGENATION CATALYSTS

(71) Applicant: NOVA Chemicals (International) S.A., Fribourg (CH)

(72) Inventors: Vasily Simanzhenkov, Calgary (CA); Xiaoliang Gao, Calgary (CA); Marie Barnes, Calgary (CA); David Sullivan, Calgary (CA); Yoonhee Kim, Calgary (CA); Perry de Wit, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 163 days.

This patent is subject to a terminal disclaimer.

(21) Appl. No.: 16/528,828

(22) Filed: Aug. 1, 2019

(65) Prior Publication Data

US 2020/0038847 A1 Feb. 6, 2020

Related U.S. Application Data

(60) Provisional application No. 62/714,274, filed on Aug. 3, 2018.

(51) Int. Cl.
*B01J 27/057* (2006.01)
*B01J 23/22* (2006.01)
(Continued)

(52) U.S. Cl.
CPC ......... *B01J 27/0576* (2013.01); *B01J 23/002* (2013.01); *B01J 23/22* (2013.01);
(Continued)

(58) Field of Classification Search
CPC combination set(s) only.
See application file for complete search history.

(56) References Cited

U.S. PATENT DOCUMENTS 5,962,757 A * 10/1999 Milam .................. B01J 23/745
502/326
8,846,996 B2 9/2014 Kustov et al.
(Continued)

FOREIGN PATENT DOCUMENTS

CA 2 655 841 A1 8/2010
DE 198 36 359 A1 3/1999
(Continued)

OTHER PUBLICATIONS

Yuan (Novel mesoporous mixed Nb—M(M=V, Mo, Sb) oxides for oxidative dehydrogenation of propane, J. Phys. Chem. B 2005, 109, 23250-23254).*
(Continued)

*Primary Examiner* — Jun Li
(74) *Attorney, Agent, or Firm* — Thomas J. Styslinger

(57) ABSTRACT

Provided in this disclosure are oxidative dehydrogenation catalysts that include a mixed metal oxide having the empirical formula:

$Mo_{1.0}V_{0.12-0.49}Te_{0.05-0.17}Nb_{0.10-0.20}O_d$ wherein d is a number to satisfy the valence of the oxide. The oxidative dehydrogenation catalyst is characterized by having XRD diffraction peaks (2θ degrees) at 22±0.2, 27±0.2, 28.0±0.2, and 28.3±0.1. The disclosure also provides methods of making the catalysts that include wet ball milling.

20 Claims, 12 Drawing Sheets

(51) Int. Cl.
 B01J 35/10 (2006.01)
 B01J 37/00 (2006.01)
 B01J 37/04 (2006.01)
 B01J 37/12 (2006.01)
 C01B 19/00 (2006.01)
 C07C 5/48 (2006.01)
 B01J 23/00 (2006.01)

(52) U.S. Cl.
 CPC ....... $B01J\ 35/1014$ (2013.01); $B01J\ 35/1038$ (2013.01); $B01J\ 37/0072$ (2013.01); $B01J\ 37/04$ (2013.01); $B01J\ 37/12$ (2013.01); $C01B\ 19/002$ (2013.01); $C07C\ 5/48$ (2013.01); $B01J\ 37/0036$ (2013.01); $B01J\ 2523/00$ (2013.01); $C01P\ 2002/50$ (2013.01); $C01P\ 2002/72$ (2013.01); $C01P\ 2006/12$ (2013.01); $C01P\ 2006/14$ (2013.01); $C07C\ 2523/20$ (2013.01); $C07C\ 2523/22$ (2013.01); $C07C\ 2523/28$ (2013.01); $C07C\ 2523/32$ (2013.01)

(56) References Cited

U.S. PATENT DOCUMENTS

| | | |
|---|---|---|
| 10,350,582 B2 | 7/2019 | Simanzhenkov et al. |
| 10,406,517 B2 | 9/2019 | Simanzhenkov et al. |
| 10,576,461 B2 | 3/2020 | Simanzhenkov et al. |
| 10,589,258 B2 | 3/2020 | Simanzhenkov et al. |
| 2004/0063990 A1* | 4/2004 | Gaffney .................. B01J 23/34 558/322 |
| 2006/0004228 A1 | 1/2006 | Hazin |
| 2010/0256432 A1* | 10/2010 | Arnold ...................... C07C 5/48 585/655 |
| 2015/0119622 A1 | 4/2015 | De Rooij et al. |
| 2018/0104675 A1 | 4/2018 | Simanzhenkov et al. |
| 2018/0200694 A1* | 7/2018 | Cadran ................ B01J 35/1023 |
| 2019/0039050 A1 | 2/2019 | Gao et al. |
| 2019/0039053 A1 | 2/2019 | Kim et al. |
| 2019/0240647 A1 | 4/2019 | Gao et al. |
| 2019/0291080 A1 | 9/2019 | Simanzhenkov et al. |

FOREIGN PATENT DOCUMENTS

| | | |
|---|---|---|
| EP | 1 080 784 A1 | 3/2001 |
| EP | 1 574 253 A2 | 9/2005 |
| WO | 2008/068332 A1 | 6/2008 |

OTHER PUBLICATIONS

Chu, Bozhao; Truter, Lara; Nijhuis, T.A. and Cheng, Yi; Performance of phase-pure M1 MoVNbTeOx catalysts by hydrothermal synthesis with different post-treatments for the oxidative dehydrogenation of ethane; Applied Catalysis A, General 438 (2015), pp. 99-106.

* cited by examiner

XRD results

OXIDATIVE DEHYDROGENATION CATALYSTS

CROSS REFERENCE TO RELATED APPLICATIONS

This application claims the benefit of the filing date of U.S. Provisional Application No. 62/714,274, which was filed on Aug. 3, 2018. The contents of U.S. Application No. 62/714,274 are incorporated by reference in their entirety as part of this application.

TECHNICAL FIELD

This disclosure relates to oxidative dehydrogenation catalysts and methods of making the catalysts.

BACKGROUND

Conversion of alkanes to olefins can be achieved in a number of ways. The most widely practiced method is thermal cracking technology, in which alkanes are exposed to temperatures of at least 700° C. for very short time periods, in the order of milliseconds to a few seconds, promoting the loss of hydrogen and the subsequent formation of one or more unsaturated bonds characteristic of olefins. However, the current thermal cracking processes are not only cost intensive to build and operate but also energy intensive due to the substantial heat requirement for the endothermic cracking reactions. Furthermore, significant amounts of $CO_2$ are produced from the operation of cracking furnaces.

Alternatively, conversion of paraffins can be accomplished using an oxidative dehydrogenation process where a stream of one or more alkanes are passed over an oxidative dehydrogenation catalyst, in the presence of oxygen or an oxygen containing gas, at temperatures from about 300° C. to 750° C. The advantages of catalytic oxidative dehydrogenation over steam cracking are that it provides higher ethane conversion and higher ethylene selectivity while using lower reaction temperatures. However, developing catalysts is difficult because olefins are more reactive than the alkanes they are derived from, creating the potential for further oxidation to unwanted byproducts. It is therefore desirable to use catalysts that are more selective for oxidation of alkanes than olefins.

SUMMARY

Provided in this disclosure is an oxidative dehydrogenation catalyst. The oxidative dehydrogenation catalyst includes a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide. The oxidative dehydrogenation catalyst is characterized by having XRD diffraction peaks (2θ degrees) at 22±0.2, 27±0.2, 28.0±0.2, and 28.3±0.1.

In some embodiments, the oxidative dehydrogenation catalyst is prepared by a process that includes wet ball milling a pretreated oxidative dehydrogenation catalyst.

In some embodiments, the aspect ratio of the peak at 27±0.2 to the peak at 22±0.2 is 0.55:1 to 0.65:1. In some embodiments, the aspect ratio of the peak at 27±0.2 to the peak at 22±0.2 is about 0.60:1. In some embodiments, the aspect ratio of the peak at 28.3±0.1 to the peak at 27±0.2 is 0.50:1 to 0.80:1. In some embodiments, the aspect ratio of the peak at 28.3±0.1 to the peak at 27±0.2 is 0.60:1 to 0.70:1. In some embodiments, the aspect ratio of the peak at 28.3±0.1 to the peak at 27±0.2 is about 0.65:1. In some embodiments, the aspect ratio of the peak at 28.0±0.2 to the peak at 28.2±0.1 is 0.8:1 to 1.1:1. In some embodiments, the aspect ratio of the peak at 28.0±0.2 to the peak at 28.2±0.1 is 0.9:1 to 1:1. In some embodiments, the aspect ratio of the peak at 28.2±0.1 to the peak at 28.4±0.2 is about 0.95:1.

In some embodiments, the oxidative dehydrogenation catalyst has a pore volume of about 0.01 $cm^3/g$ to about 0.10 $cm^3/g$. For example, the oxidative dehydrogenation catalyst can have a pore volume of about 0.06 $cm^3/g$ to about 0.08 $cm^3/g$. In some embodiments, the oxidative dehydrogenation catalyst has a pore volume of about 0.07 $cm^3/g$.

In some embodiments, the oxidative dehydrogenation catalyst has a surface area of about 15 $m^2/g$ to about 65 $m^2/g$. For example, the oxidative dehydrogenation catalyst can have a surface area of about 35 $m^2/g$ to about 45 $m^2/g$. In some embodiments, the oxidative dehydrogenation catalyst has a surface area of about 40 $m^2/g$.

In some embodiments, the oxidative dehydrogenation catalyst includes multi-directional crystalline phases as determined by transmission electron microscopy (TEM).

In some embodiments, the oxidative dehydrogenation catalyst has a 35% conversion temperature of about 335° C. to about 395° C. For example, the oxidative dehydrogenation catalyst can have a 35% conversion temperature of about 355° C. to about 365° C.

In some embodiments, the oxidative dehydrogenation catalyst has a selectivity to ethylene of greater than about 90%. For example, the oxidative dehydrogenation catalyst can have a selectivity to ethylene of greater than about 92%. In some embodiments, the oxidative dehydrogenation catalyst has a selectivity to ethylene of greater than about 93.5%.

Also provided in this disclosure is an oxidative dehydrogenation catalyst that includes a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide. The oxidative dehydrogenation catalyst is characterized by having XRD diffraction peaks (2θ degrees) at 22±0.2, 27±0.2, 28.0±0.2, and 28.3±0.1. The aspect ratio of the peak at 27±0.2 to the peak at 22±0.2 is 0.50:1 to 0.70:1, the aspect ratio of the peak at 28.3±0.1 to the peak at 27±0.2 is 0.50:1 to 0.80:1, and the aspect ratio of the peak at 28.0±0.2 to the peak at 28.2±0.1 is 0.8:1 to 1.1:1. The oxidative dehydrogenation catalyst has a 35% conversion temperature of about 335° C. to about 395° C. and a selectivity to ethylene of about 90% to about 99%. Further, the oxidative dehydrogenation catalyst is prepared by wet ball milling a pretreated oxidative dehydrogenation catalyst that includes a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide.

Additionally, provided in this disclosure is an oxidative dehydrogenation catalyst that includes a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide. The oxidative dehydrogenation catalyst is characterized by having XRD diffraction peaks (2θ degrees) at 22±0.2, 27±0.2, 28.0±0.2, and 28.3±0.1. The aspect ratio of the peak at 27±0.2 to the peak at 22±0.2 is 0.55:1 to 0.65:1. The aspect ratio of the peak at 28.3±0.1 to the peak at 27±0.2 is 0.60:1 to 0.70:1. The aspect ratio of the peak at 28.0±0.2 to the peak at 28.2±0.1 is 0.9:1 to 1:1. The oxidative dehydrogenation catalyst has a 35% conversion temperature of about 355° C. to about 365° C. and a selectivity to ethylene of about 92% to about 99%. Further, the oxidative dehydrogenation catalyst is prepared by wet ball milling a pretreated oxidative dehydrogenation catalyst that includes a mixed metal oxide having the empirical formula:

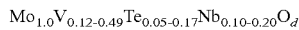
$Mo_{1.0}V_{0.12-0.49}Te_{0.05-0.17}Nb_{0.10-0.20}O_d$ wherein d is a number to satisfy the valence of the oxide.

Also provided in this disclosure is a method for the formation of an oxidative dehydrogenation catalyst comprising a mixed metal oxide having the empirical formula:

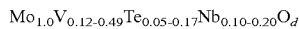
$Mo_{1.0}V_{0.12-0.49}Te_{0.05-0.17}Nb_{0.10-0.20}O_d$ wherein d is a number to satisfy the valence of the oxide. The method includes providing a mixture including a pretreated oxidative dehydrogenation catalyst and a water. The method further includes wet ball milling the mixture to provide the oxidative dehydrogenation catalyst.

In some embodiments, the method further includes providing the pretreated oxidative dehydrogenation catalyst. Providing the pretreated oxidative dehydrogenation catalyst can include calcining a pre-calcined oxidative dehydrogenation catalyst to provide the pretreated oxidative dehydrogenation catalyst.

In some embodiments, the pre-calcined oxidative dehydrogenation catalyst is calcined in an inert atmosphere at a temperature of about 450° C. to about 650° C. For example, the pre-calcined oxidative dehydrogenation catalyst can be calcined in an inert atmosphere at a temperature of about 600° C. In some embodiments, the pre-calcined oxidative dehydrogenation catalyst is calcined in an inert atmosphere for about 1 hour to about 3 hours. For example, the pre-calcined oxidative dehydrogenation catalyst can be calcined in an inert atmosphere for about 2 hours. In some embodiments, the pre-calcined oxidative dehydrogenation catalyst is calcined in an inert atmosphere at a temperature of about 500° C. to about 700° C. for about 1 hour to about 3 hours. For example, the pre-calcined oxidative dehydrogenation catalyst can be calcined in an inert atmosphere at a temperature of about 600° C. for about 2 hours.

In some embodiments, the method increases the amorphous phase of the oxidative dehydrogenation catalyst about 5 wt. % to about 15 wt. % as compared to the pretreated oxidative dehydrogenation catalyst. For example, the method can increase the amorphous phase of the oxidative dehydrogenation catalyst about 10 wt. %.

DETAILED DESCRIPTION

Figure 1:
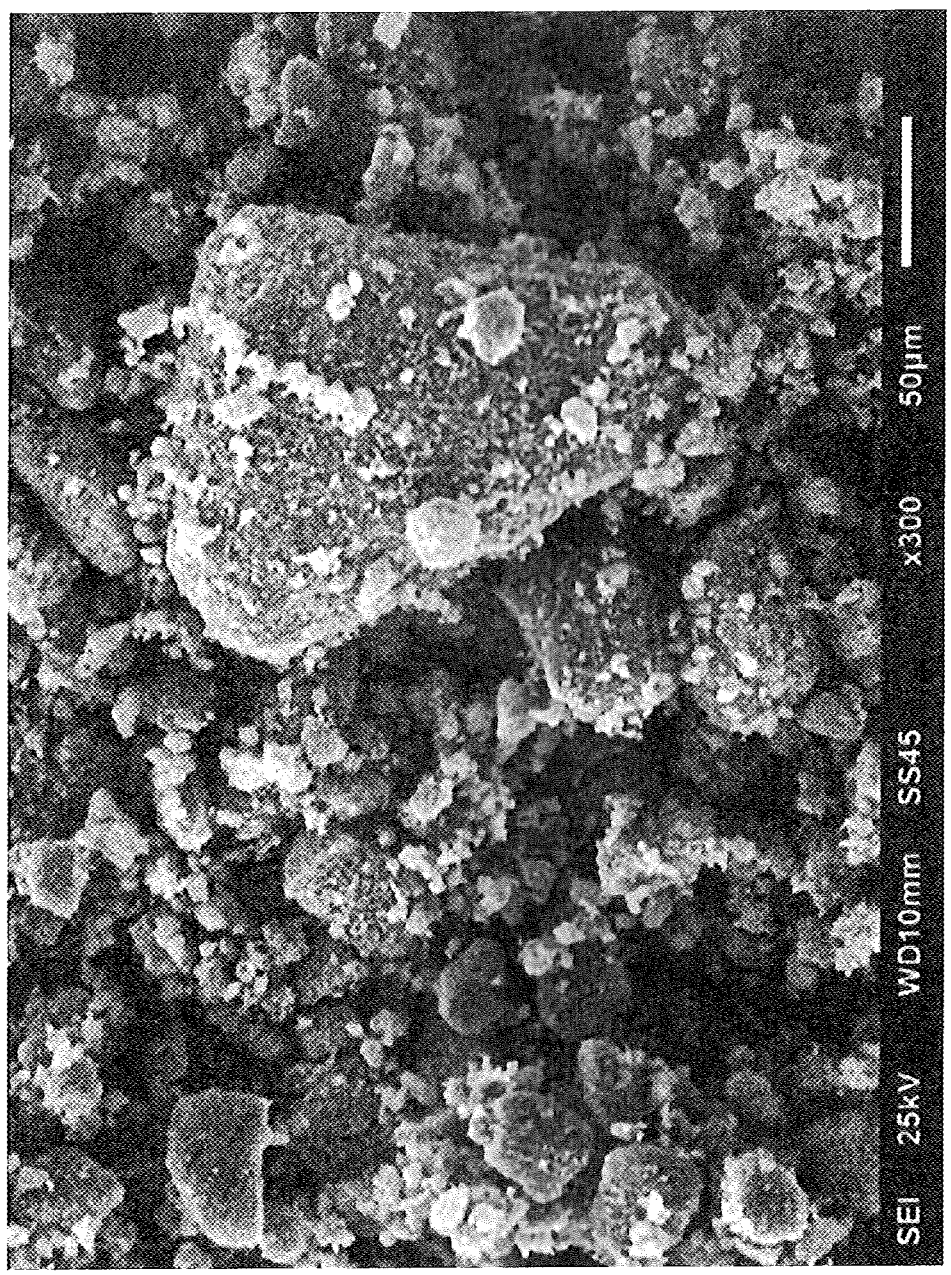
FIG. 1 is a (scanning electron microscope) SEM image of an oxidative dehydrogenation catalyst (Catalyst 1.1) before wet ball milling.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "room temperature" as used herein refers to a temperature of about 15° C. to about 28° C.

Provided in this disclosure is an oxidative dehydrogenation catalyst. The oxidative dehydrogenation catalyst includes a mixed metal oxide having the empirical formula:

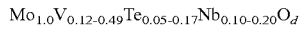

$Mo_{1.0}V_{0.12-0.49}Te_{0.05-0.17}Nb_{0.10-0.20}O_d$ wherein d is a number to satisfy the valence of the oxide. Further, the catalyst is characterized by having XRD diffraction peaks (2θ degrees) at least at 22±0.2, 27±0.2, 28.0±0.2, and 28.3±0.1, wherein the XRD is obtained using CuKα radiation.

In some embodiments, the mixed metal oxide has the empirical formula $Mo_{1.0}V_{0.22-0.49}Te_{0.10-0.17}Nb_{0.14-0.17}O_d$. In some embodiments, the mixed metal oxide has the empirical formula $Mo_{1.0}V_{0.25-0.38}Te_{0.10-0.16}Nb_{0.15-0.19}O_d$. The empirical formula can be measured by particle induced X-ray emission (PIXE) analysis.

The oxidative dehydrogenation catalyst can be prepared by wet ball milling. Wet ball milling is a mechanochemical technique that can be used for grinding materials into particles.

The aspect ratio of the peak at 27±0.2 to the peak at 22±0.2 can be 0.50:1 to 0.70:1 or 0.55:1 to 0.65:1, wherein the XRD is obtained using CuKα radiation. For example, the aspect ratio of the peak at 27±0.2 to the peak at 22±0.2 can be about 0.60:1, wherein the XRD is obtained using CuKα radiation.

It should be understood that the oxidative dehydrogenation catalyst disclosed herein are not limited to those that provide XRD patterns that are identical to the XRD patterns shown in the Figures, and that any catalyst compositions providing XRD patterns substantially the same as those shown in the Figures fall within the scope of the corresponding embodiment. A person skilled in the art of XRD is able to judge the substantial identity of XRD patterns. Generally, a measurement error of a diffraction angle in an XRD is approximately 2θ (±0.2° or ±0.1°), and such degree of a measurement error should be taken into account when considering the X-ray diffraction pattern in the Figures and when reading data contained in the Tables included herein.

The aspect ratio of the peak at 28.3±0.1 to the peak at 27±0.2 can be 0.50:1 to 0.80:1 or 0.60:1 to 0.70:1, wherein the XRD is obtained using CuKα radiation. For example, the aspect ratio of the peak at 28.3±0.1 to peak the peak at 27±0.2 can be about 0.65:1, wherein the XRD is obtained using CuKα radiation.

The aspect ratio of the peak at 28.0±0.2 to the peak at 28.2±0.1 can be 0.8:1 to 1.1:1 or 0.9:1 to 1:1, wherein the XRD is obtained using CuKα radiation. For example, the aspect ratio of the peak at 28.2±0.1 to the peak at 28.3±0.1 can be about 0.95:1, wherein the XRD is obtained using CuKα radiation.

In some embodiments, the aspect ratio of the peak at 27±0.2 to the peak at 22±0.2 is 0.50:1 to 0.70:1, the aspect ratio of the peak at 28.3±0.1 to the peak at 27±0.2 is 0.50:1 to 0.80:1, and the aspect ratio of the peak at 28.0±0.2 to the peak at 28.2±0.1 is 0.8:1 to 1.1:1, wherein the XRD is obtained using CuKα radiation. In some embodiments, the aspect ratio of the peak at 27±0.2 to the peak at 22±0.2 is 0.55:1 to 0.65:1, the aspect ratio of the peak at 28.3±0.1 to the peak at 27±0.2 is 0.60:1 to 0.70:1, and the aspect ratio of the peak at 28.0±0.2 to the peak at 28.2±0.1 is 0.9:1 to 1:1, wherein the XRD is obtained using CuKα radiation. For example, the aspect ratio of the peak the peak at 27±0.2 to the peak at 22±0.2 can be about 0.60:1, the aspect ratio of the peak at 28.3±0.1 to peak the peak at 27±0.2 can be about 0.65:1, and the aspect ratio of the peak at 28.2±0.1 to the peak at 28.3±0.1 can be about 0.95:1, wherein the XRD is obtained using CuKα radiation.

The oxidative dehydrogenation catalyst can have a pore volume from about 0.01 $cm^3/g$ to about 0.10 $cm^3/g$, about 0.05 $cm^3/g$ to about 0.10 $cm^3/g$, or from about 0.06 $cm^3/g$ to about 0.08 $cm^3/g$. For example, the oxidative dehydrogenation catalyst can have a pore volume of about 0.07 $cm^3/g$. The pore volume of the oxidative dehydrogenation catalyst can be measured by Brunauer-Emmett-Teller (BET) surface area analysis using ASTM D3663.

In some embodiments, the oxidative dehydrogenation catalyst has a surface area from about 15 $m^2/g$ to about 65 $m^2/g$, about 25 $m^2/g$ to about 55 $m^2/g$, or from about 35 $m^2/g$ to about 45 $m^2/g$. For example, the oxidative dehydrogenation catalyst can have a surface area of about 35 $m^2/g$, 40 $m^2/g$, or about 45 $m^2/g$. As used herein, the term "surface area" refers to specific surface area as determined by BET using ASTM D3663 including adsorption-desorption of nitrogen, with a liquid nitrogen temperature of −196° C. and degassing at 200° C. for 1 h prior to the adsorption. In some embodiments, the oxidative dehydrogenation catalyst has a surface area from about 15 $m^2/g$ to about 65 $m^2/g$, about 25 $m^2/g$ to about 55 $m^2/g$, or from about 35 $m^2/g$ to about 45 $m^2/g$, as determined by nitrogen adsorption (e.g., nitrogen adsorption at −196° C.) by BET. For example, the oxidative dehydrogenation catalyst can have a surface area of about 35 $m^2/g$, about 40 $m^2/g$, or about 45 $m^2/g$ as determined by nitrogen adsorption (e.g., nitrogen adsorption at −196° C.) by BET.

Figure 4:
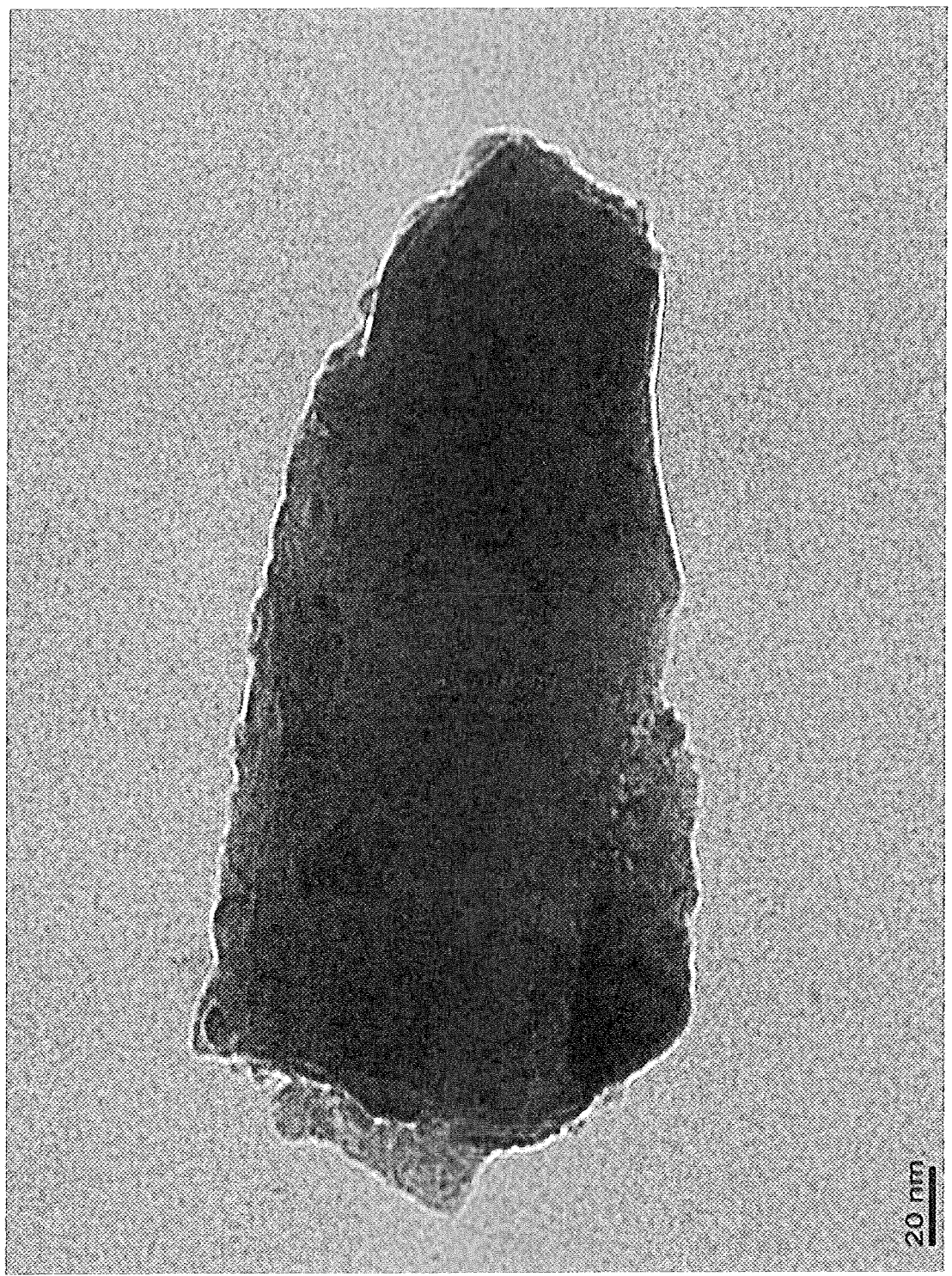
FIG. 4 is a TEM image of a wet ball milled oxidative dehydrogenation catalyst (Catalyst 1.2) showing the multidirectional crystalline phases and smaller size nanoparticles.
Figure 5:
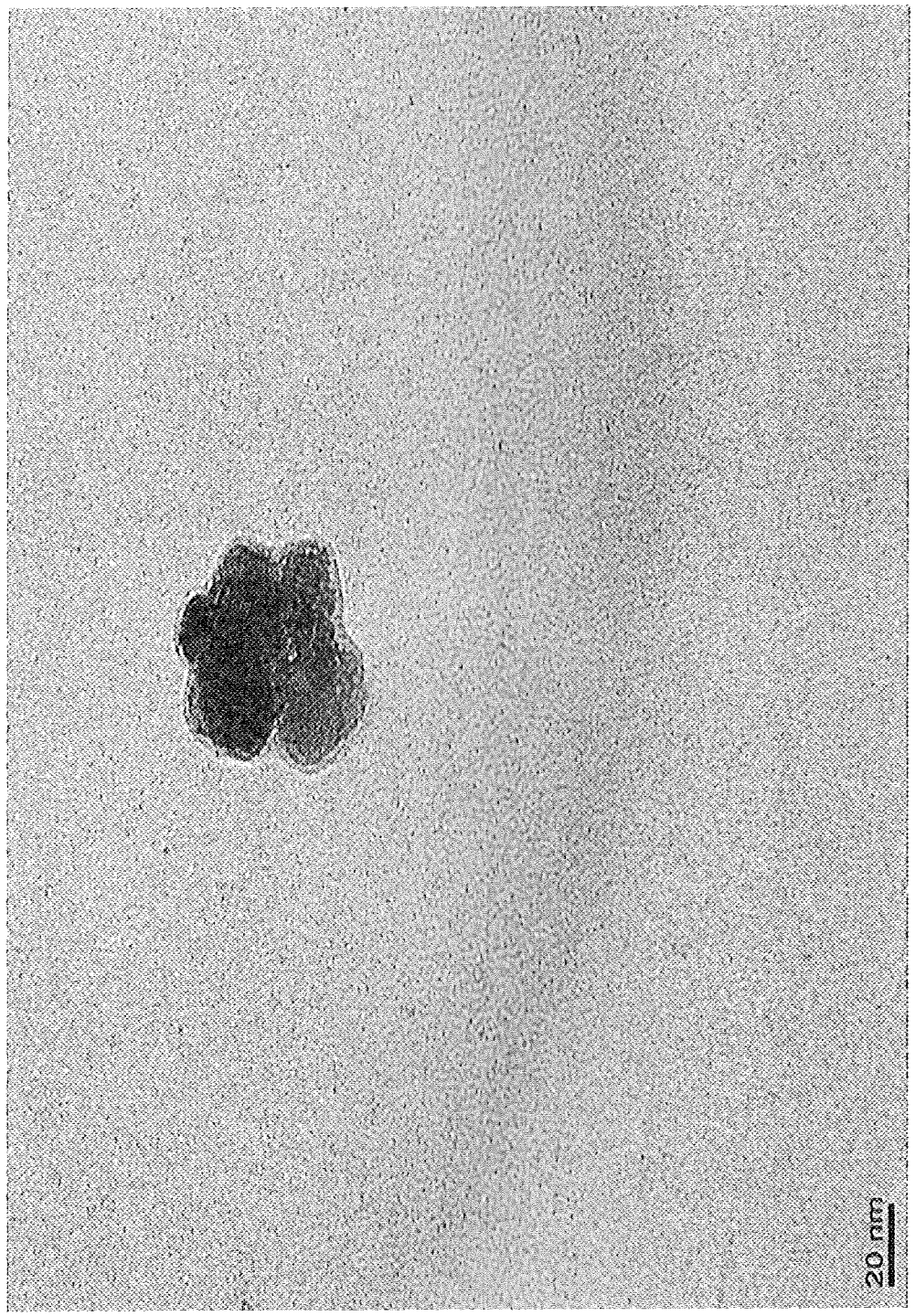
FIG. 5 is a TEM image of a wet ball milled oxidative dehydrogenation catalyst (Catalyst 1.2) showing the multidirectional crystalline phases.

In some embodiments, the oxidative dehydrogenation catalyst includes a multi-directional crystalline phase as determined by transmission electron microscopy (TEM). For example, the oxidative dehydrogenation catalyst can have an irregular shape (e.g., a non-needle like or non-rod like shape). Examples of oxidative dehydrogenation catalysts produced by wet ball milling having an irregular shape are shown in FIGS. 4 and 5.

In some embodiments, the oxidative dehydrogenation catalyst has a 35% conversion temperature from about 335° C. to about 395° C., about 345° C. to about 385° C., or about 355° C. to about 365° C. For example, the oxidative dehydrogenation catalyst can have a 35% conversion temperature of about 355° C., 360° C., or about 365° C.

As used in this disclosure, the phrase "35% conversion temperature" refers to the temperature at which 35% of ethane in a gas stream is converted to a product other than ethane. The 35% conversion temperature of an oxidative dehydrogenation catalyst can be determined by using a microreactor unit (MRU). In a microreactor unit, the 35% conversion temperature of a catalyst can be determined by passing a feed gas over a catalyst bed in a reactor tube. The MRU reactor tube has an outer diameter of about 0.5 inches and an internal diameter of about 0.4 inches and length of about 15 inches. For example, the reactor tube can be stainless-steel SWAGELOK® Tubing with a wall thickness of about 0.049 inches. The feed gas can include ethane and oxygen having a molar ratio of 70:30 to 90:10. For example, the feed gas can include ethane and oxygen having a molar ratio of 82:18. Alternatively, the feed gas can include ethane, oxygen, and nitrogen. The molar ratio of ethane to oxygen to nitrogen can be 18:18:64 to 54:18:28. For example, the molar ratio of ethane to oxygen to nitrogen can be 36:18:46 or 35:17.5:47.5. The flow rate of the feed gas can be about 70 standard cubic centimeters per minute (sccm) to about 80 sccm. For example, the flow rate of the feed gas can be about 75 sccm (e.g., 74.6 sccm). The catalyst bed consists of the oxidative dehydrogenation catalyst and a filler, such as sand, in a one to one volume ratio, with the total weight for the oxidative dehydrogenation catalyst being 1.96 g. Any remaining space in the reactor tube (e.g., below or above the catalyst bed) is packed with an additional filler, such as quartz sand. The 35% conversion temperature is determined at a weight hourly space velocity (WHSV) of 2.90 h$^{-1}$, with the WHSV based on the active phase, and a gas hourly space velocity (GHSV) of about 2,000 to 3,000 h$^{-1}$. Typically, the inlet pressure is in the range of about 1 pound per square inch gauge (psig) to about 2.5 psig and the outlet pressure is in the range of about 0 psig to about 0.5 psig. The gas feed exiting the catalyst bed is analyzed by gas chromatography to determine the percent of various hydrocarbons (e.g., ethane and ethylene) and, optionally other gases such as $O_2$, $CO_2$, and CO. Conversion of the feed gas is calculated as a mass flow rate change of ethane in the product compared to feed ethane mass flow rate using the following formula:

$$C = \left( \frac{2 * X_{Ethylene} + X_{CO2} + X_{CO}}{2 * X_{Ethylene} + X_{Ethane} + X_{CO2} + X_{CO}} \right) * 100\%$$

wherein C is the percent of feed gas that has been converted from ethane to another product (i.e., ethane conversion) and X is the molar concentration of the corresponding compound in the gaseous effluent exiting the reactor. The ethane conversion is then plotted as a function of temperatures to acquire a linear algebraic equation. The linear equation for ethane conversion is solved to determine the temperature in which the ethane conversion is 35% (i.e. the 35% conversion temperature). Not taken into account for calculating the 35% conversion temperature or selectivity to ethane, described below, were reaction products exiting the reactor in an aqueous stream such as, but not limited to, acetic acid, maleic acid, propionic acid, ethanol, and acetaldehyde.

In some embodiments, the oxidative dehydrogenation catalyst has a 35% conversion temperature from about 335° C. to about 395° C., about 345° C. to about 385° C., or from about 355° C. to about 365° C. under MRU testing as described herein with a feed gas of ethane, oxygen, and nitrogen at molar ratio of 35:17.5:47.5 and a flow rate of about 75 sccm. For example, the oxidative dehydrogenation catalyst can have a 35% conversion temperature of about 355° C., 360° C., or about 365° C., under MRU testing as described herein with a feed gas of ethane, oxygen, and nitrogen at molar ratio of 35:17.5:47.5 and a flow rate of about 75 sccm.

The oxidative dehydrogenation catalyst can have a selectivity to ethylene of greater than about 90%. For example, the oxidative dehydrogenation catalyst can have a selectivity to ethylene of about 90% to about 99% or about 90% to about 95%. As used in this disclosure, the phrase "selectivity to ethylene" refers to the percentage on a molar basis of converted or reacted ethane that forms ethylene. An oxidative dehydrogenation catalyst's selectivity to ethylene can be determined using an MRU as discussed above. An oxidative dehydrogenation catalyst's selectivity to ethylene can be determined using to the following equation:

$$S_{Ethylene} = \left( \frac{2 * X_{Ethylene}}{2 * X_{Ethylene} + X_{CO2} + X_{CO}} \right) * 100\%$$

wherein $S_{Ethylene}$ is the selectivity to ethylene, and X is the molar concentration of the corresponding compound in the gaseous effluent exiting the reactor. Notably, the selectivity to ethylene is determined at the 35% conversion temperature, unless otherwise indicated. As such, after the 35% conversion temperature is determined, the above equation for selectivity is solved using the corresponding values for $X_{Ethylene}$, $X_{CO_2}$, and $X_{CO}$ at the 35% conversion temperature.

In some embodiments, the oxidative dehydrogenation catalyst has a selectivity to ethylene of greater than about 92%. For example, the oxidative dehydrogenation catalyst can have a selectivity to ethylene of about 92% to about 99% or about 92% to about 95%. In some embodiments, the oxidative dehydrogenation catalyst has a selectivity to ethylene of greater than about 93.5%. For example, the oxidative dehydrogenation catalyst can have a selectivity to ethylene of about 93.5% to about 99% or about 93.5% to about 95%.

In some embodiments, the oxidative dehydrogenation catalyst has a 35% conversion temperature of about 335° C. to about 395° C. and a selectivity to ethylene of about 90% to about 99% under MRU testing as described herein with a feed gas of ethane, oxygen, and nitrogen at molar ratio of 35:17.5:47.5 and a flow rate of about 75 sccm. For example, the oxidative dehydrogenation catalyst can have a 35% conversion temperature from about 345° C. to about 385° C. and a selectivity to ethylene from about 92% to about 99% under MRU testing as described herein with a feed gas of ethane, oxygen, and nitrogen at molar ratio of 35:17.5:47.5 and a flow rate of about 75 sccm. The oxidative dehydrogenation catalyst can also have a 35% conversion temperature from about 355° C. to about 365° C. and a selectivity to ethylene from about 92% to about 99% under MRU testing as described herein with a feed gas of ethane, oxygen, and nitrogen at molar ratio of 35:17.5:47.5 and a flow rate of about 75 sccm.

Also provided in this disclosure is an oxidative dehydrogenation catalyst that is prepared by a process that includes wet ball milling a pretreated oxidative dehydrogenation catalyst. The pretreated oxidative dehydrogenation catalyst includes a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide. The oxidative dehydrogenation catalyst includes a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide. The oxidative dehydrogenation catalyst is characterized by having XRD diffraction peaks (2θ degrees) at 22±0.2, 27±0.2, 28.0±0.2, and 28.3±0.1, wherein the XRD is obtained using CuKα radiation. The aspect ratio of the peak at 27±0.2 to the peak at 22±0.2 is 0.50:1 to 0.70:1, the aspect ratio of the peak at 28.3±0.1 to the peak at 27±0.2 is 0.50:1 to 0.80:1, and the aspect ratio of the peak at 28.0±0.2 to the peak at 28.2±0.1 is 0.8:1 to 1.1:1. The oxidative dehydrogenation catalyst has a 35% conversion temperature from about 335° C. to about 395° C. and a selectivity to ethylene from about 90% to about 99%. For example, the oxidative dehydrogenation catalyst can have a 35% conversion temperature from about 335° C. to about 395° C. and a selectivity to ethylene from about 90% to about 99% under MRU testing as described herein with a feed gas of ethane, oxygen, and nitrogen at molar ratio of 35:17.5:47.5 and a flow rate of about 75 sccm.

Further provided in this disclosure is an oxidative dehydrogenation catalyst that is prepared by a process that includes wet ball milling a pretreated oxidative dehydrogenation catalyst. The oxidative dehydrogenation catalyst includes a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide. The oxidative dehydrogenation catalyst is characterized by having XRD diffraction peaks (2θ degrees) at 22±0.2, 27±0.2, 28.0±0.2, and 28.3±0.1, wherein the XRD is obtained using CuKα radiation. The aspect ratio of the peak at 27±0.2 to the peak at 22±0.2 is 0.55:1 to 0.65:1, the aspect ratio of the peak at 28.3±0.1 to the peak at 27±0.2 is 0.60:1 to 0.70:1, and the aspect ratio of the peak at 28.0±0.2 to the peak at 28.2±0.1 is 0.9:1 to 1:1. The oxidative dehydrogenation catalyst has a 35% conversion temperature from about 355° C. to about 365° C. and a selectivity to ethylene from about 92% to about 99%. For example, the oxidative dehydrogenation catalyst can have a 35% conversion temperature of about 355° C. to about 365° C. and a selectivity to ethylene of about 92% to about 99% under MRU testing as described herein with a feed gas of ethane, oxygen, and nitrogen at molar ratio of 35:17.5:47.5 and a flow rate of about 75 sccm.

In some embodiments, the oxidative dehydrogenation catalyst has a surface area from about 35 m²/g to about 45 m²/g.

Also provided in this disclosure is a method for preparing an oxidative dehydrogenation catalyst including a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide. The method includes providing a mixture that includes a pretreated oxidative dehydrogenation catalyst and a water, and wet ball milling the mixture to provide the oxidative dehydrogenation catalyst.

In some embodiments, the pretreated oxidative dehydrogenation catalyst includes a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide. The pretreated oxidative dehydrogenation catalyst can be prepared as described in U.S. Publication No. 20170050178A1, the disclosure of which is incorporated herein by reference in its entirety.

In some embodiments, the mixed metal oxide of the pretreated oxidative dehydrogenation catalyst has the empirical formula $Mo_{1.0}V_{0.22-0.49}Te_{0.10-0.17}Nb_{0.14-0.17}O_d$. In some embodiments, the mixed metal oxide of the pretreated oxidative dehydrogenation catalyst has the empirical formula $Mo_{1.0}V_{0.22-0.38}Te_{0.10-0.16}Nb_{0.15-0.19}O_d$. The empirical formula can be measured by particle induced X-ray emission (PIXE) analysis.

In some embodiments, providing the mixture including the pretreated oxidative dehydrogenation catalyst and the water can further include providing the pretreated oxidative dehydrogenation catalyst. Providing the pretreated oxidative dehydrogenation catalyst can include calcining a pre-calcined oxidative dehydrogenation catalyst to provide the pretreated oxidative dehydrogenation catalyst. The pre-calcined oxidative dehydrogenation catalyst can be calcined in an inert atmosphere at a temperature from about 450° C. to about 650° C. For example, the pre-calcined oxidative dehydrogenation catalyst can be calcined in an inert atmosphere at a temperature of about 600° C. In some embodiments, the pre-calcined oxidative dehydrogenation catalyst is calcined in an inert atmosphere for about 1 hour to about 3 hours. For example, the pre-calcined oxidative dehydrogenation catalyst can be calcined in an inert atmosphere for about 2 hours. In some embodiments, the pre-calcined oxidative dehydrogenation catalyst is calcined in an inert atmosphere at a temperature from about 500° C. to about 700° C. for about 1 hour to about 3 hours. For example, the pre-calcined oxidative dehydrogenation catalyst can be calcined in an inert atmosphere at a temperature of about 600° C. for about 2 hours.

The water in the mixture can be selected from distilled water, deionized water, demineralized water, mineral water, or a combination thereof. In some embodiments, the water includes distilled water.

The volume ratio of the calcined oxidative dehydrogenation catalyst to the water to balls (e.g., 3 mm zirconium calls) during wet ball milling can be 0.5-3.0:0.25-2.0:1.0-3.0. In some embodiments, the volume ratio of the calcined oxidative dehydrogenation catalyst to water to balls during wet ball milling is 1.0-2.0:0.5-2.5:1.5:2.5. For example, the volume ratio of the calcined oxidative dehydrogenation catalyst to water to balls (e.g., 3 mm zirconium calls) can be about 1.5:1.9:1.75.

In some embodiments, the pretreated oxidative dehydrogenation catalyst is wet ball milled until further wet ball milling does not result in a further change in particle size distribution. In some embodiments, the pretreated oxidative dehydrogenation catalyst is wet ball milled until the desired increase in 35% conversion temperature is obtained.

Wet ball milling can increase the amorphous phase of the oxidative dehydrogenation catalyst by about 5 wt. % to about 15 wt. % as compared to the pretreated oxidative dehydrogenation catalyst that the oxidative dehydrogenation catalyst is prepared from. For example, wet ball milling can increase the amorphous phase of the oxidative dehydrogenation catalyst by about 5 wt. % to about 15 wt. % as compared to the pretreated oxidative dehydrogenation catalyst prior to wet ball milling.

In some embodiments, a binder can be added to the mixture including the pretreated oxidative dehydrogenation catalyst and the water. In some embodiments, a binder can be added to the oxidative dehydrogenation catalyst after wet ball milling. In some embodiments, a binder can be added to the mixture including the pretreated oxidative dehydrogenation catalyst and the water and again after the wet ball milling step.

The binder can be an alumina, a titanium compound, a zirconia, or a combination thereof. The alumina can be an aluminum oxide hydroxide, such a boehmite, a an aluminum oxide, or a combination thereof. In some embodiments, the boehmite is a pseudoboehmite such as VERSAL™ 250. VERSAL™ 250 has a dispersibility index (%<1 mu) of 20-30, a bulk density of 12-16 pounds per cubic foot (lbs/ft$^3$), a surface area of about 320 meters squared per gram (m$^2$/g), and a loss on ignition (LOI) of about 26 wt. %. The dispersibility index for VERSAL™ 250 can be determined by using 8 grams of sample on a volatile free basis and 96 milliliters (mL) of 0.22 normal (N) nitric acid solution, which is approximately 260 meq nitric acid per 100 grams (g) of alumina, mixing the acidic alumina slurry in a WARING® blender at low speed (17000 rpm) for 5 min, and then determining particle size distribution by using a SEDI-GRAPH® PSA—with the results reported as wt. % submicron particles. The adjuvant can also be the boehmite CATAPAL® B. CATAPAL® B is an alumina hydrate that has a loose bulk density of 670 to 750 g/L, a packed bulk density of 800 to 1100 g/L, a particle size (d$_{50}$) of 60 μm, a surface area (BET) after activation at 550° C. for 3 hours of 250 m$^2$/g, a pore volume after activation at 550° C. for 3 hours of 0.5 ml/g, and a crystallite size (120) of about 4.5 nm.

Also provided herein is a method for the oxidative dehydrogenation of ethane to ethylene in an oxidative dehydrogenation reactor with any oxidative dehydrogenation catalysts described herein.

Ethylene can subsequently be converted into a variety of products. For example, ethylene can be converted into many various compounds including low density polyethylene, high density polyethylene, ethylene dichloride, ethylene oxide, ethylbenzene, linear alcohols, vinyl acetate, alkanes, alpha olefins, various hydrocarbon-based fuels, ethanol and the like. These compounds can then be further processed using methods well known to one of ordinary skill in the art to obtain other valuable chemicals and consumer products.

Embodiments disclosed herein include, but are not limited to:

Embodiment A: An oxidative dehydrogenation catalyst that includes a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide, and the oxidative dehydrogenation catalyst is characterized by having XRD diffraction peaks (2θ degrees) at 22±0.2, 27±0.2, 28.0±0.2, and 28.3±0.1.

Embodiment A can have one or more of the following additional elements in any combination:

Element A1: Wherein the catalyst is prepared by a process that includes wet ball milling a pretreated oxidative dehydrogenation catalyst having the empirical formula:

$$Mo_{1.0}V_{0.12-0.49}Te_{0.05-0.17}Nb_{0.10-0.20}O_d$$

wherein d is a number to satisfy the valence of the oxide.

Element A2: Wherein the aspect ratio of the peak at 27±0.2 to the peak at 22±0.2 is 0.55:1 to 0.65:1.

Element A3: Wherein the aspect ratio of the peak at 27±0.2 to the peak at 22±0.2 is about 0.60:1.

Element A4: Wherein the aspect ratio of the peak at 28.3±0.1 to the peak at 27±0.2 is 0.50:1 to 0.80:1.

Element A5: Wherein the aspect ratio of the peak at 28.3±0.1 to the peak at 27±0.2 is 0.60:1 to 0.70:1.

Element A6: Wherein the aspect ratio of the peak at 28.3±0.1 to the peak at 27±0.2 is about 0.65:1.

Element A7: Wherein the aspect ratio of the peak at 28.0±0.2 to the peak at 28.2±0.1 is 0.8:1 to 1.1:1.

Element A8: Wherein the aspect ratio of the peak at 28.0±0.2 to the peak at 28.2±0.1 is 0.9:1 to 1:1.

Element A9: Wherein the aspect ratio of the peak at 28.2±0.1 to the peak at 28.4±0.2 is about 0.95:1.

Element A10: Wherein the catalyst has a pore volume from about 0.01 cm$^3$/g to about 0.10 cm$^3$/g.

Element A11: Wherein the catalyst has a pore volume from about 0.06 cm$^3$/g to about 0.08 cm$^3$/g.

Element A12: Wherein the catalyst has a pore volume of about 0.07 cm$^3$/g.

Element A13: Wherein the catalyst has a surface area from about 15 m$^2$/g to about 65 m$^2$/g.

Element A14: Wherein the catalyst has a surface area from about 35 m$^2$/g to about 45 m$^2$/g.

Element A15: Wherein the catalyst has a surface area of about 40 m$^2$/g.

Element A16: Wherein the catalyst includes multi-directional crystalline phases as determined by transmission electron microscopy.

Element A17: Wherein the catalyst has a 35% conversion temperature of about 335° C. to about 395° C.

Element A18: Wherein the catalyst has a 35% conversion temperature of about 355° C. to about 365° C.

Element A19: Wherein the catalyst has a selectivity to ethylene of greater than about 90%.

Element A20: Wherein the catalyst has a selectivity to ethylene of greater than about 92%.

Element A21: Wherein the catalyst has a selectivity to ethylene of greater than about 93.5%.

Element A22: Wherein the catalyst further includes Nb$_{0.5}$V$_{0.5}$O$_2$.

By way of non-limiting example, exemplary element combinations applicable to Embodiment A include: A2, A4, and A7; A10 and A13; A2, A4, A10, and A13; and the like.

Embodiment B: An oxidative dehydrogenation catalyst that includes a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide; the oxidative dehydrogenation catalyst is characterized by having XRD diffraction peaks (2θ degrees) at 2210.2, 27±0.2, 28.0±0.2, and 28.3±0.1; the aspect ratio of the peak at 27±0.2 to the peak at 22±0.2 is 0.50:1 to 0.70:1, the aspect ratio of the peak at 28.3±0.1 to the peak at 27±0.2 is 0.50:1 to 0.80:1, and the aspect ratio of the peak at 28.0±0.2 to the peak at 28.2±0.1 is 0.8:1 to 1.1:1; the oxidative dehydrogenation catalyst has a 35% conversion temperature of about 335° C. to about 395° C. and a selectivity to ethylene of about 90% to about 99%; and the catalyst is prepared by a process including wet ball milling a pretreated oxidative dehydrogenation catalyst having the empirical formula:

$$Mo_{1.0}V_{0.12-0.49}Te_{0.05-0.17}Nb_{0.10-0.20}O_d$$

wherein d is a number to satisfy the valence of the oxide.

Embodiment C: An oxidative dehydrogenation catalyst that includes a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide; the oxidative dehydrogenation catalyst is characterized by having XRD diffraction peaks (2θ degrees) at 22±0.2, 27±0.2, 28.0±0.2, and 28.3±0.1; the aspect ratio of the peak at 27±0.2 to the peak at 22±0.2 is 0.55:1 to 0.65:1, the aspect ratio of the peak at 28.3±0.1 to the peak at 27±0.2 is 0.60:1 to 0.70:1, and the aspect ratio of the peak at 28.0±0.2 to the peak at 28.2±0.1 is 0.9:1 to 1:1; the oxidative dehydrogenation catalyst has a 35% conversion temperature of about 355° C. to about 365° C. and a selectivity to ethylene of about 92% to about 99%; and the oxidative dehydrogenation catalyst is prepared by a process including wet ball milling a pretreated oxidative dehydrogenation catalyst having the empirical formula:

$$Mo_{1.0}V_{0.12-0.49}Te_{0.05-0.17}Nb_{0.10-0.20}O_d$$

wherein d is a number to satisfy the valence of the oxide.

Embodiment D: A method for preparing an oxidative dehydrogenation catalyst that includes a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide, wherein the method includes providing a mixture including a pretreated oxidative dehydrogenation catalyst and a water, and wet ball milling the mixture to provide the oxidative dehydrogenation catalyst.

Embodiment D can have one or more of the following additional elements in any combination:

Element D1: Wherein pretreated oxidative dehydrogenation catalyst has the empirical formula:

$$Mo_{1.0}V_{0.12-0.49}Te_{0.05-0.17}Nb_{0.10-0.20}O_d$$

wherein d is a number to satisfy the valence of the oxide.

Element D2: Wherein the method further includes providing the pretreated oxidative dehydrogenation catalyst.

Element D3: Wherein the method further includes providing the pretreated oxidative dehydrogenation catalyst; and wherein providing the pretreated oxidative dehydrogenation catalyst includes calcining a pre-calcined oxidative dehydrogenation catalyst.

Element D4: Wherein the method further includes providing the pretreated oxidative dehydrogenation catalyst; and wherein providing the pretreated oxidative dehydrogenation catalyst includes calcining a pre-calcined oxidative dehydrogenation catalyst; and wherein calcining includes calcining the pre-calcined oxidative dehydrogenation catalyst in an inert atmosphere at a temperature of about 450° C. to about 650° C.

Element D5: Wherein the method further includes providing the pretreated oxidative dehydrogenation catalyst; and wherein providing the pretreated oxidative dehydrogenation catalyst includes calcining a pre-calcined oxidative dehydrogenation catalyst; and wherein calcining includes calcining the pre-calcined oxidative dehydrogenation catalyst in an inert atmosphere at a temperature of about 600° C.

Element D6: Element D4: Wherein the method further includes providing the pretreated oxidative dehydrogenation catalyst; and wherein providing the pretreated oxidative dehydrogenation catalyst includes calcining a pre-calcined oxidative dehydrogenation catalyst; and wherein calcining includes calcining the pre-calcined oxidative dehydrogenation catalyst in an inert atmosphere for about 1 hour to about 3 hours.

Element D7: Wherein the method further includes providing the pretreated oxidative dehydrogenation catalyst; and wherein providing the pretreated oxidative dehydrogenation catalyst includes calcining a pre-calcined oxidative dehydrogenation catalyst; and wherein calcining includes calcining the pre-calcined oxidative dehydrogenation catalyst in an inert atmosphere for about 2 hours.

Element D8: Wherein the method further includes providing the pretreated oxidative dehydrogenation catalyst; and wherein providing the pretreated oxidative dehydrogenation catalyst includes calcining a pre-calcined oxidative dehydrogenation catalyst; and wherein calcining the catalyst includes calcining the pre-calcined oxidative dehydrogenation catalyst in an inert atmosphere at a temperature of about 500° C. to about 700° C. for about 1 hour to about 3 hours.

Element D9: Wherein the method further includes providing the pretreated oxidative dehydrogenation catalyst; and wherein providing the pretreated oxidative dehydrogenation catalyst includes calcining a pre-calcined oxidative dehydrogenation catalyst; and wherein calcining includes calcining the pre-calcined oxidative dehydrogenation catalyst in an inert atmosphere at a temperature of about 600° C. for about 2 hours.

Element D10: Wherein the method increases the amorphous phase of the catalyst about 5 wt. % to about 15 wt. %.

Element D11: Wherein the method increases the amorphous phase of the catalyst about 10 wt. %.

By way of non-limiting example, exemplary element combinations applicable to Embodiment D include: D1 and D2; D1 and D10; and the like.

EXAMPLES

Example 1.1

520 grams (g) of preprocessed oxidative dehydrogenation catalysts including molybdenum, vanadium, tellurium, niobium, and oxygen, wherein the catalysts had molar ratios in the range of $Mo_{1.0}V_{0.12-0.49}Te_{0.05-0.17}Nb_{0.10-0.20}O_d$, as determined by PIXE, were transferred to a catalyst calcination furnace (CCF) for calcination. Calcination included a first step of 48 hours of nitrogen purging prior to heating, increasing the temperature from room temperature to 600° C. over a period of six-hours, and maintaining the 600° C. temperature for two hours to yield the calcined oxidative dehydrogenation catalyst, Catalyst 1.1, having the empirical formula $Mo_{1.0}V_{0.12-0.49}Te_{0.05-0.17}Nb_{0.10-0.20}O_d$.

The activity and selectivity of the Catalyst 1.1 was determined using an MRU, as disclosed herein. The activity and selectivity results are presented in Table 1 of Example 1.8. Further, the pore volume and BET surface area were measured and the results are presented in Table 1 of Example 1.8.

Figure 2:
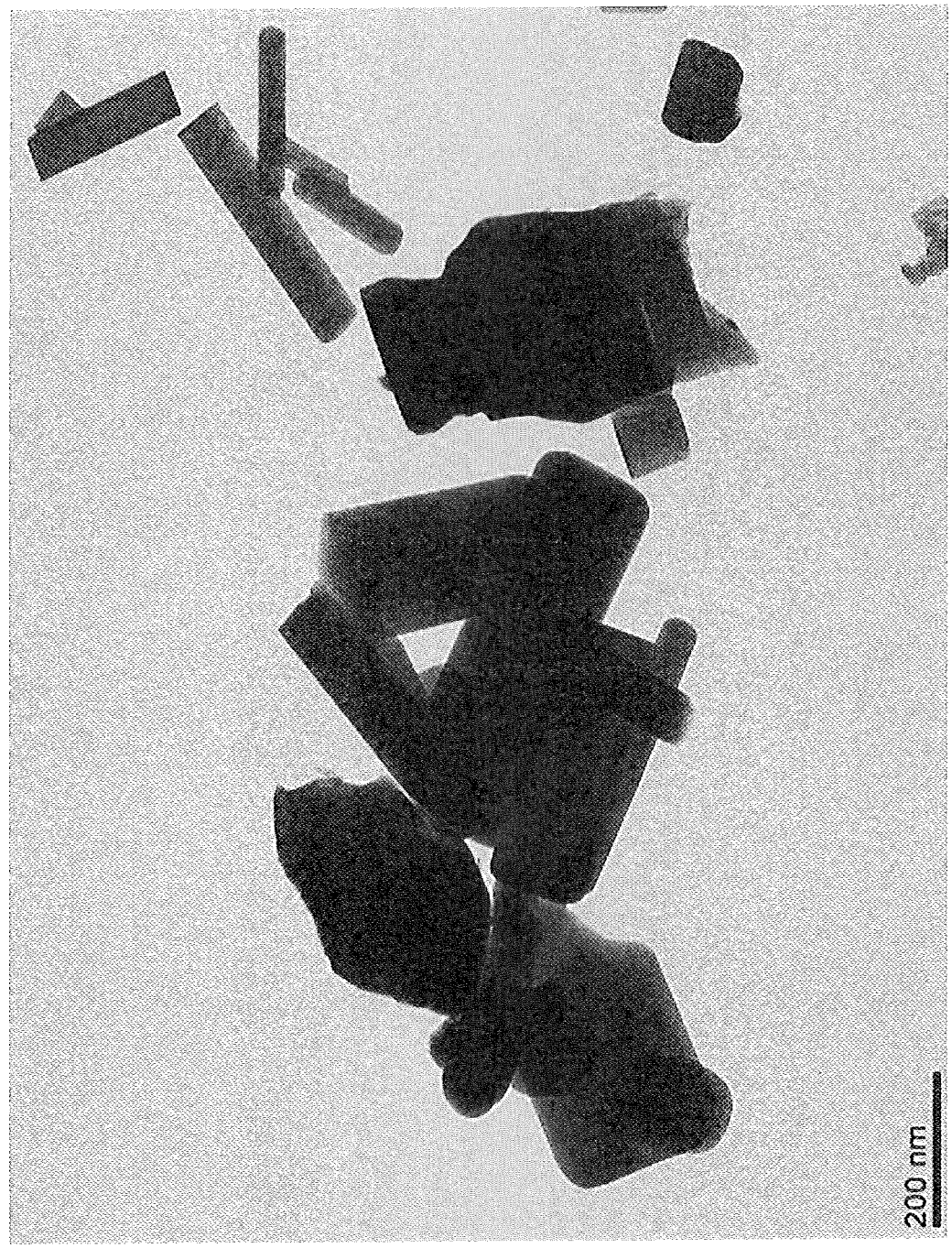
FIG. 2 is a transmission electron microscope (TEM) image of an oxidative dehydrogenation catalyst (Catalyst 1.1) before wet ball milling.
Figure 3:
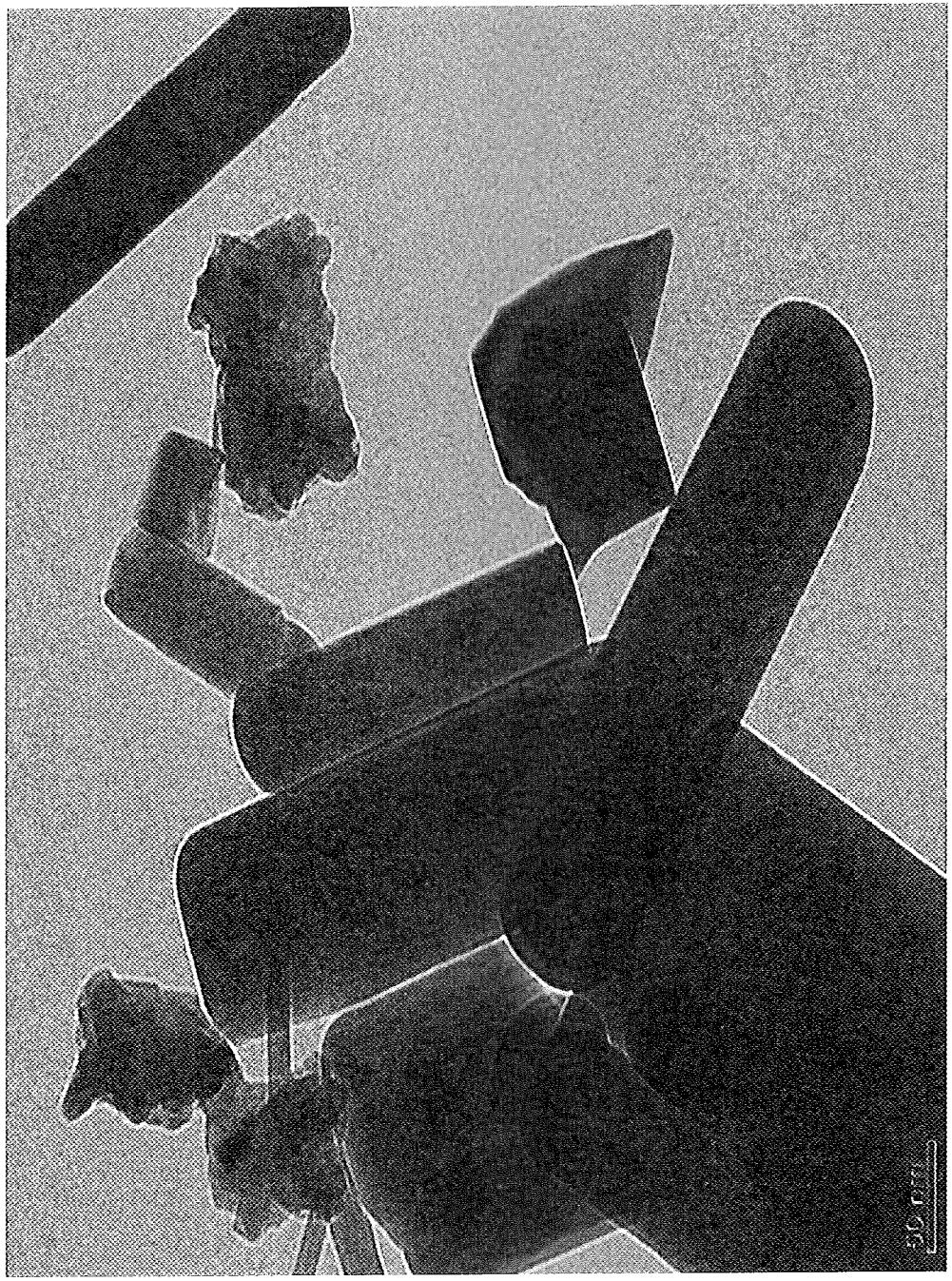
FIG. 3 is a TEM image of an oxidative dehydrogenation catalyst (Catalyst 1.1) before wet ball milling, magnified by 100×.

A scanning electron microscope (SEM) image of Catalyst 1.1 is shown in FIG. 1. Transmission electron microscope (TEM) images of Catalyst 1.1 are shown in FIGS. 2 and 3.

Example 1.2

In a ball mill zirconium chamber, 150 mL of Catalyst 1.1 was combined with 100 mL of water and 175 mL of 3 mm zirconia balls. Catalyst 1.1 was then wet ball milled for 2 hours at 400 rpm. After wet ball milling, the mixture was taken out and placed on a sieve to separate zirconia balls and washed with more water. Around 2 liters (L) of the mixture containing the catalyst was then placed in a fume hood to settle and dry for one month at room temperature to yield Catalyst 1.2.

The activity and selectivity of Catalyst 1.2 was determined using an MRU, as disclosed herein. The activity and selectivity results are presented in Table 1 of Example 1.8.

Further, the pore volume and BET surface area were measured and the results are presented in Table 1 of Example 1.8.

TEM images of Catalyst 1.2 are shown in FIGS. 4 and 5. As can be seen in FIGS. 4 and 5, the oxidative dehydrogenation catalysts have an irregular shape (e.g., a non-needle like or non-rod like shape).

Example 1.3

Approximately 145 g of an oxidative dehydrogenation catalyst having the empirical formula $Mo_{1.0}V_{0.12-0.49}Te_{0.05-0.17}Nb_{0.10-0.20}O_d$ was added to a grinding chamber. Approximately 648 g of 3 mm zirconium oxide balls were also placed in the 500 mL zirconium oxide grinding chamber. 400 mL of water was then added to the grinding chamber to make a watery paste and it was stirred manually to make it consistent. The grinding chamber was placed in the ball mill instrument and clamped tight. The weight of the chamber and the content was 8.26 kilograms (kg). The wet ball milling was then performed at 400 rpm for 2 hours with a half hour pause after 1 hour. After the run was completed, the grinding chamber was opened in a fume hood. The content was removed and approximately 800 mL of water was added to separate the balls from the catalyst. Subsequently, the wet catalyst was oven dried at 90° C. and the dried catalyst was manually ground with mortar and pestle to yield Catalyst 1.3.

The activity and selectivity of Catalyst 1.3 was determined using an MRU, as disclosed herein. The activity and selectivity results are presented in Table 1 of Example 1.8.

Example 1.4

Catalyst 1.3 was agitated and sub-sampled in 20 mL hypo-vial and centrifuged for 30 minutes. The liquid was then decanted and vacuum pumped for one hour to remove moisture yielding around 3 g, which was collected and ground with a mortar and pestle to yield Catalyst 1.4.

Figure 6:
FIG. 6, is an SEM image of a wet ball milled and centrifuged oxidative dehydrogenation catalyst (Catalyst 1.4).

The activity and selectivity of Catalyst 1.4 was determined using an MRU, as disclosed herein. The activity and selectivity results are presented in Table 1 of Example 1.8. A SEM image of Catalyst 1.4 is shown in FIG. 6.

Example 1.5

10.48 g of Catalyst 1.1 was place in a centrifuge tube and 150 mL of distilled water. Subsequently, the tube was sonicated in a sonication bath for 60 minutes. After sonication, the particles appeared to be completely suspended in the water giving the water a dark purple color. The dark purple suspended solids were centrifuged down using a centrifuge. Next, the particles were dried on a high vacuum/nitrogen line to yield the Catalyst 1.5.

The activity and selectivity of the oxidative dehydrogenation catalyst v was determined using an MRU, as disclosed herein. The activity and selectivity results are presented in Table 1 of Example 1.8. Further, the pore volume and BET surface area were measured and the results are also presented in Table 1 of Example 1.8.

Example 1.6

Approximately 500 g of the Catalyst 1.1 was ground five times, one minute per grind, using a blade grinder to yield Catalyst 1.6.

The activity and selectivity of Catalyst 1.6 was determined using an MRU, as disclosed herein. The activity and selectivity results are presented in Table 1 of Example 1.8. The pore volume and BET surface area were measured and the results are also presented in Table 1 of Example 1.8.

Figure 7:
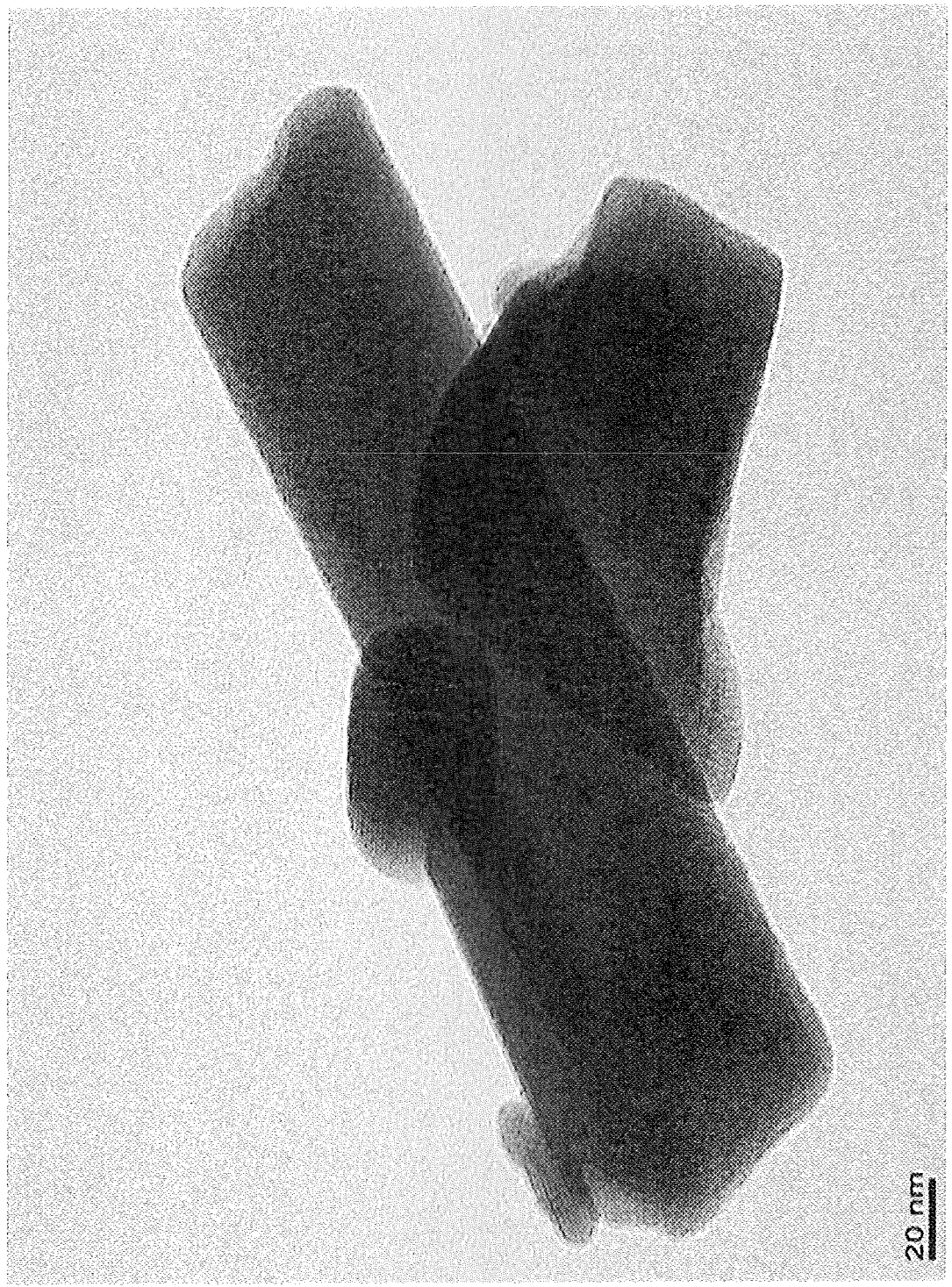
FIG. 7 is a TEM image of an oxidative dehydrogenation catalyst ground by a blade grinder, (Catalyst 1.6) showing crystalline striations in the resulting nanosized material.
Figure 8:
FIG. 8 is a TEM image of an oxidative dehydrogenation catalyst ground by a blade grinder (Catalyst 1.6) showing crystalline striations in the resulting nanosized material.
Figure 9:
FIG. 9 is a TEM image of an oxidative dehydrogenation catalyst ground by a blade grinder, (Catalyst 1.6) showing crystalline striations in the resulting nanosized material.

TEM images of Catalyst 1.6 are shown in FIGS. 7, 8, and 9.

Example 1.7

Approximately 175 mL (648 g) of 3 mm zirconium oxide balls were placed in a 500 mL zirconium oxide grinding chamber. Approximately 150 mL (100 g) of Catalyst 1.1 was added to the grinding chamber. The grinder chamber was then placed in the ball mill instrument and clamped tight; the weight of the chamber and the contents was 8.12 kg. The ball mill was operated at 400 rpm for 2 hours with a ½ hour pause after 1 hour. After the run was completed, the grinding chamber was allowed to cool to room temperature. The chamber was the opened in a fume hood. The product was deposited on the outside wall of the grinding chamber and chipped out of the grinding chamber to yield Catalyst 1.7.

Example 1.8

The 35% conversion temperature and selectivity of the oxidative dehydrogenation catalysts of Examples 1.1-1.6 were determined using an MRU as described herein. The feed gas composition entering the reactor tube was 35% ethane, 17.5% oxygen, and 47.5% nitrogen. The WHSV based on the active phase was 2.90 $h^{-1}$. The flow rate of the feed gas was about 74.6 sccm. The 35% conversion temperature and selectivity of the oxidative dehydrogenation catalysts of Examples 1.1-1.6 are presented in Table 1.

The BET surface ($m^2/g$) and pore volume ($cm^3/g$) for the catalyst of Examples 1.1, 1.2, and 1.5-1.7 were measured as follows. ASTM D3663 was used to determine surface area and the total pore volume was calculated by $N_2$ uptake at the relative pressure $P/P_0=0.99$. BET surface ($m^2/g$) and pore volume ($cm^3/g$) for the catalyst of Examples 1.1, 1.2, and 1.5-1.7 are presented in Table 1.

TABLE 1

| Catalyst | 35% Conversion Temp. (° C.) | Selectivity to Ethylene | BET surface ($m^2/g$) | pore volume ($cm^3/g$) |
|---|---|---|---|---|
| Catalyst 1.1 | 386 | 95.4% | 7 | 0.02 |
| Catalyst 1.2 | 360 | 93% | 42 | 0.07 |
| Catalyst 1.3 | 363 | 94% | — | — |
| Catalyst 1.4 | 357 | 93.8% | — | — |
| Catalyst 1.5 | 389 | 95% | 10 | 0.03 |
| Catalyst 1.6 | 380 | 95% | 9 | 0.02 |
| Catalyst 1.7 | 382 | 92% | 10 | 0.04 |

As shown in Table 1, wet ball milling increased the surface area and pore volume of the oxidative dehydrogenation catalyst. Specifically, the surface area increased from 7 $m^2/g$ for the baseline oxidative dehydrogenation catalyst to 42 $m^2/g$ for the wet ball milled oxidative dehydrogenation catalyst while the pore volume increased from 0.02 cm³/g for the baseline catalyst to 0.07 cm³/g for the wet ball milled catalyst. Further, the wet ball milled oxidative dehydrogenation catalyst had a lower 35% conversion temperature of 360° C. when compared to the 386° C. 35% conversion temperature of the baseline oxidative dehydrogenation catalyst. In comparison, sonication also increased the surface area and pore volume—however, the 35% conversion temperature increased by 3° C. to 389° C.

Figure 10:
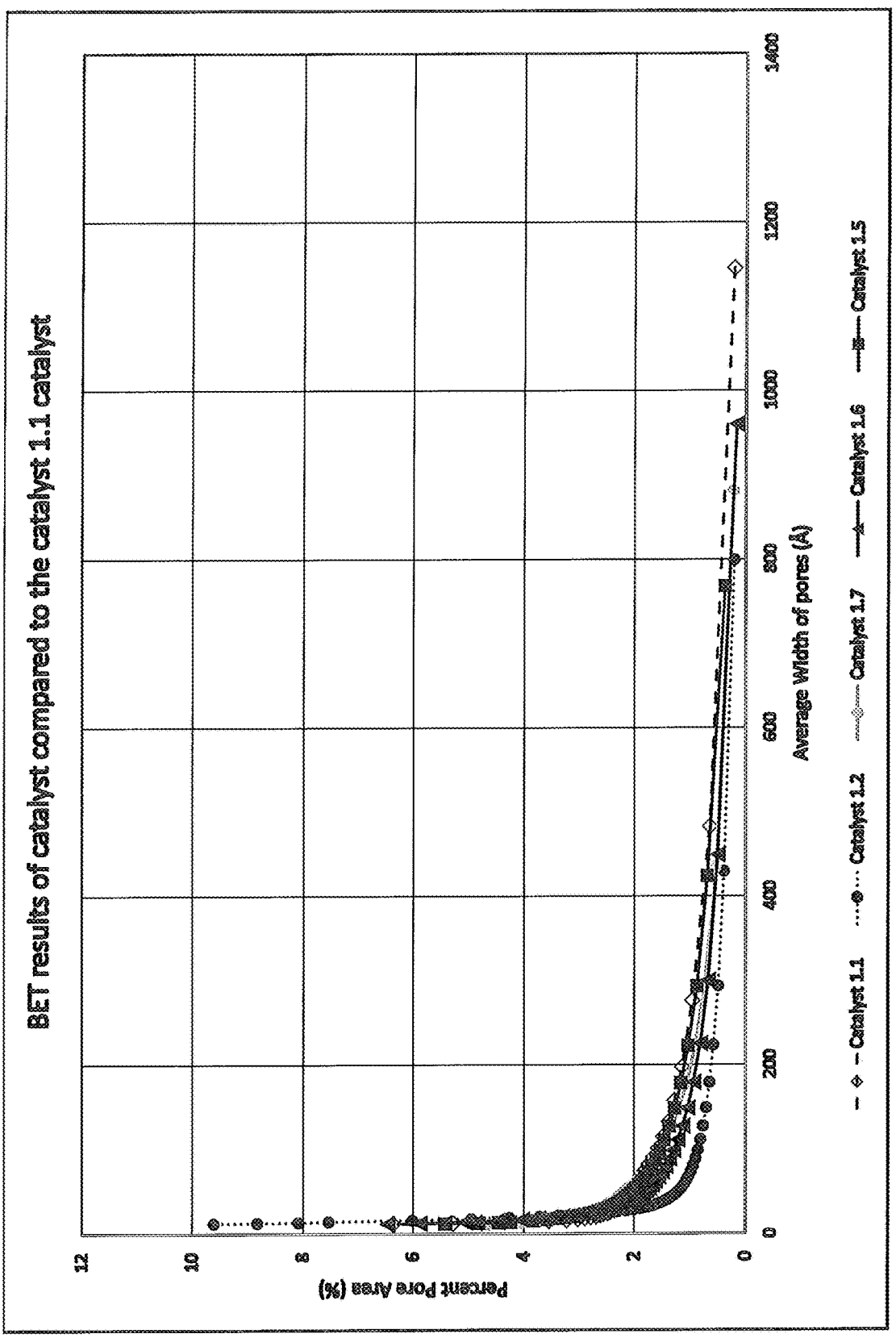
FIG. 10 is a BET overlay of an oxidative dehydrogenation catalyst (Catalyst 1.1), a wet ball milled oxidative dehydrogenation catalyst (Catalyst 1.2), a sonicated oxidative dehydrogenation catalyst (Catalyst 1.5), an oxidative dehydrogenation catalyst ground by a blade grinder (Catalyst 1.6), and a dry ball milled oxidative dehydrogenation catalyst (Catalyst 1.7).

Further, a BET overlay of the baseline oxidative dehydrogenation catalyst (Catalyst 1.1), the wet ball milled oxidative dehydrogenation catalyst (Catalyst 1.2), the sonicated baseline oxidative dehydrogenation catalyst (Catalyst 1.5), the blade ground oxidative dehydrogenation catalyst (Catalyst 1.6), and the dry ball milled oxidative dehydrogenation catalyst is presented in FIG. 10. Surprisingly, as shown in FIG. 10, the pore structure of the wet ball milled oxidative dehydrogenation catalyst has changed, as one can see form the figure above. Additionally, FIG. 10 confirms that wet ball milled oxidative dehydrogenation catalyst underwent a crystalline and physical change during the wet ball milling process.

Example 1.9

The XRD patterns for the catalysts of Examples 1.1, 1.2, and 1.5-1.7 were obtained as follows. A portion of each catalyst was finely crushed and ground using a mortar and pestle in preparation for XRD analysis. XRD was employed to identify and quantify the phases present in the sample. A known amount of corundum was added as internal standard to determine the weight percentage of the amorphous portion. From the overestimation of the standard phase a correction factor was calculated, which was in turn applied to all crystalline phases. The remaining difference to 100% (after applying the correction factor) was determined to be the weight percentage of the missing (i.e. amorphous) phase(s). The XRD data was collected using a PANalytical Aeris X-ray diffractometer. Qualitative XRD analysis and Rietveld Refinement was performed using HighScore Plus XRD analysis software.

Figure 11:
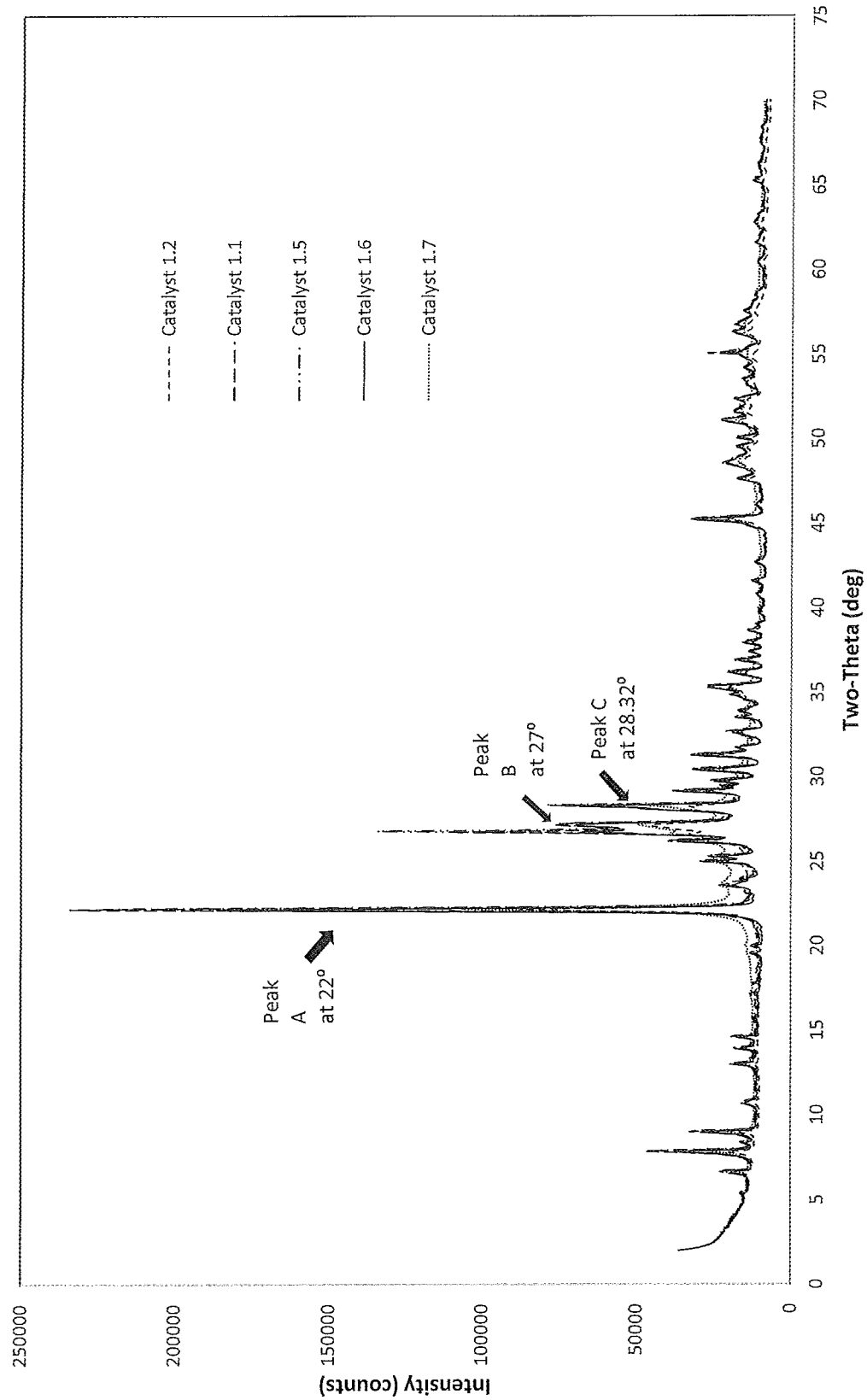
FIG. 11 is an overlay of the XRD patterns for an oxidative dehydrogenation catalyst (Catalyst 1.1), a wet ball milled oxidative dehydrogenation catalyst (Catalyst 1.2), a sonicated oxidative dehydrogenation catalyst (Catalyst 1.5), a blade ground oxidative dehydrogenation catalyst (Catalyst 1.6), and a dry ball milled oxidative dehydrogenation catalyst (Catalyst 1.7).
Figure 12:
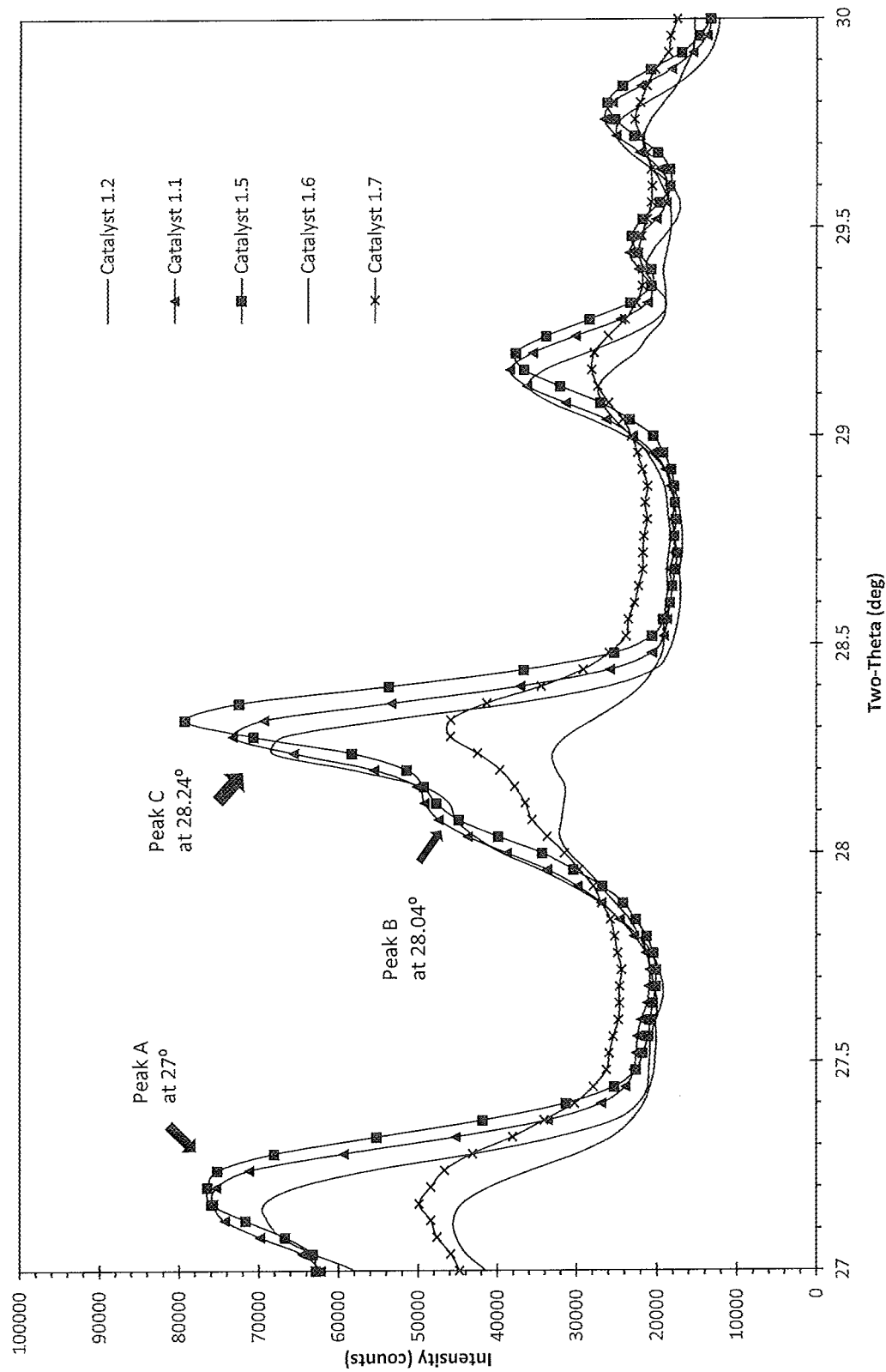
FIG. 12 is an overlay of the XRD patterns for an oxidative dehydrogenation catalyst (Catalyst 1.1), a wet ball milled oxidative dehydrogenation catalyst (Catalyst 1.2), a sonicated oxidative dehydrogenation catalyst (Catalyst 1.5), a blade ground oxidative dehydrogenation catalyst (Catalyst 1.6), and a dry ball milled oxidative dehydrogenation catalyst (Catalyst 1.7).

An overlay of the XRD patterns for Examples 1.1, 1.2, 1.5, 1.6, and 1.7 are shown in FIG. 11. An additional overlay of the XRD patterns for Examples 1.1, 1.2, 1.5, 1.6, and 1.7 is shown in FIG. 12.

A Table comparing the relative intensities of the peaks at 22±0.2, 27±0.2, 28.0±0.2 and 28.3±0.1 is presented below in Table 2.

TABLE 2

| | Ratio of the intensity of XRD Peaks | | | |
|---|---|---|---|---|
| | 27°:22° | 28.24°:27° | 28.04°:28.24° | 35% Conv. Temp./Sel. |
| Catalyst 1.1 | 0.34:1.0 | 0.96:1.0 | 0.58:1.0 | 386° C./95.4% |
| Catalyst 1.2 | 0.59:1.0 | 0.64:1.0 | 0.95:1.0 | 357° C./95% |
| Catalyst 1.5 | 0.35:1.0 | 1.04:1.0 | 0.50:1.0 | 389° C./95% |
| Catalyst 1.6 | 0.39:1.0 | 0.96:1.0 | 0.61:1.0 | 380° C./95% |
| Catalyst 1.7 | 0.53:1.0 | 0.90:1.0 | 0.69:1.0 | 382° C./92% |

Notably, only the wet ball milled oxidative dehydrogenation catalyst had XRD results with an aspect ratio between the peak at 27 (2θ degrees) to 22 (2θ degrees) of 0.59:1. Further, the double peak between 28.04° (2θ degrees) and 28.24° (2θ degrees) can play important role in high activity (e.g., a lower 35% conversion temperature) as it is evident that the 28.04 (2θ degrees) peak becomes more intense when compared to the pick 28.24 (2θ degrees) for the wet ball milled oxidative dehydrogenation catalyst. Specifically, the aspect ratio between the peak at 28.04° (2θ degrees) and 28.24° (2θ degrees) is 0.95:1.0 for wet ball milled sample whereas the other non-wet ball milled oxidative dehydrogenation catalysts (e.g., Examples 1.1, 1.5, 1.6, 1.7) have aspect ratios of 0.50-69:1.0. Similarly, the aspect ratio between 28.24 (2θ degrees) and 27 (2θ degrees) can play an important role in high activity (e.g. a lower 35% conversion temperature). The aspect ratio between 28.24 (2θ degrees) and 27 (2θ degrees) for the wet ball milled oxidative dehydrogenation catalyst is 0.64:1 (i.e. Peak C was 64% of Peak B) whereas the non-wet ball milled oxidative dehydrogenation catalyst were in the range of 0.90-1.04:1.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An oxidative dehydrogenation catalyst comprising a mixed metal oxide having the empirical formula:

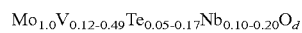

$$Mo_{1.0}V_{0.12-0.49}Te_{0.05-0.17}Nb_{0.10-0.20}O_d$$

wherein:
   d is a number to satisfy the valence of the oxide,
   the oxidative dehydrogenation catalyst is characterized by having XRD diffraction peaks (2θ degrees) at 22±0.2, 27±0.2, 28.0±0.2, and 28.3±0.1,
   the oxidative dehydrogenation catalyst has a pore volume from 0.01 cm³/g to 0.10 cm³/g, and
   the oxidative dehydrogenation catalyst has a surface area from 15 m²/g to 65 m²/g.

2. The oxidative dehydrogenation catalyst of claim 1, wherein the catalyst is prepared by a process comprising wet ball milling a pretreated oxidative dehydrogenation catalyst having the empirical formula:

$$Mo_{1.0}V_{0.12-0.49}Te_{0.05-0.17}Nb_{0.10-0.20}O_d$$

wherein d is a number to satisfy the valence of the oxide.

3. The oxidative dehydrogenation catalyst of claim 1, wherein the aspect ratio of the peak at 27±0.2 to the peak at 22±0.2 is 0.55:1 to 0.65:1.

4. The oxidative dehydrogenation catalyst of claim 1, wherein the aspect ratio of the peak at 27±0.2 to the peak at 22±0.2 is about 0.60:1.

5. The oxidative dehydrogenation catalyst of claim 1, wherein the aspect ratio of the peak at 28.3±0.1 to the peak at 27±0.2 is 0.50:1 to 0.80:1.

6. The oxidative dehydrogenation catalyst of claim 1, wherein the aspect ratio of the peak at 28.3±0.1 to the peak at 27±0.2 is 0.60:1 to 0.70:1.

7. The oxidative dehydrogenation catalyst of claim 1, wherein the aspect ratio of the peak at 28.3±0.1 to the peak at 27±0.2 is about 0.65:1.

8. The oxidative dehydrogenation catalyst of claim 1, wherein the catalyst has a pore volume of about 0.06 cm³/g to about 0.08 cm³/g.

9. The oxidative dehydrogenation catalyst of claim 1, wherein the catalyst has a pore volume of about 0.07 cm³/g.

10. The oxidative dehydrogenation catalyst of claim 1, wherein the catalyst has a surface area from 35 m²/g to 45 m²/g.

11. The oxidative dehydrogenation catalyst of claim 1, wherein the catalyst has a surface area of about 40 m²/g.

12. The oxidative dehydrogenation catalyst of claim 1, wherein the catalyst comprises multi-directional crystalline phases as determined by transmission electron microscopy.

13. The oxidative dehydrogenation catalyst of claim 1, wherein the catalyst has a 35% conversion temperature of about 335° C. to about 395° C.

14. The oxidative dehydrogenation catalyst of claim 1, wherein the catalyst has a 35% conversion temperature of about 355° C. to about 365° C.

15. The oxidative dehydrogenation catalyst of claim 1, wherein the catalyst has a selectivity to ethylene of greater than about 90%.

16. The oxidative dehydrogenation catalyst of claim 1, wherein the catalyst has a selectivity to ethylene of greater than about 92%.

17. The oxidative dehydrogenation catalyst of claim 1, wherein the catalyst has a selectivity to ethylene of greater than about 93.5%.

18. The oxidative dehydrogenation catalyst of claim 1, wherein the catalyst further comprises $Nb_{0.5}V_{0.5}O_2$.

19. An oxidative dehydrogenation catalyst comprising a mixed metal oxide having the empirical formula:

$$Mo_{1.0}V_{0.12-0.49}Te_{0.05-0.17}Nb_{0.10-0.20}O_d$$

wherein:
   d is a number to satisfy the valence of the oxide,
   the oxidative dehydrogenation catalyst is characterized by having XRD diffraction peaks (2θ degrees) at 22±0.2, 27±0.2, 28.0±0.2, 28.2±0.1, and 28.3±0.1,
   the aspect ratio of the peak at 27±0.2 to the peak at 22±0.2 is 0.50:1 to 0.70:1, the aspect ratio of the peak at 28.3±0.1 to the peak at 27±0.2 is 0.50:1 to 0.80:1, and the aspect ratio of the peak at 28.0±0.2 to the peak at 28.2±0.1 is 0.8:1 to 1.1:1,
   the oxidative dehydrogenation catalyst has a 35% conversion temperature of about 335° C. to about 395° C. and a selectivity to ethylene of about 90% to about 99%,
   the catalyst is prepared by a process comprising wet ball milling a pretreated oxidative dehydrogenation catalyst having the empirical formula:

$$Mo_{1.0}V_{0.12-0.49}Te_{0.05-0.17}Nb_{0.10-0.20}O_d$$

wherein d is a number to satisfy the valence of the oxide,
   the oxidative dehydrogenation catalyst has a pore volume from 0.01 cm³/g to 0.10 cm³/g, and
   the oxidative dehydrogenation catalyst has a surface area from 15 m²/g to 65 m²/g.

20. An oxidative dehydrogenation catalyst comprising a mixed metal oxide having the empirical formula:

$$Mo_{1.0}V_{0.12-0.49}Te_{0.05-0.17}Nb_{0.10-0.20}O_d$$

wherein:
   d is a number to satisfy the valence of the oxide,
   the oxidative dehydrogenation catalyst is characterized by having XRD diffraction peaks (2θ degrees) at 22±0.2, 27±0.2, 28.0±0.2, 28.2±0.1, and 28.3±0.1,
   the aspect ratio of the peak at 27±0.2 to the peak at 22±0.2 is 0.55:1 to 0.65:1, the aspect ratio of the peak at 28.3±0.1 to the peak at 27±0.2 is 0.60:1 to 0.70:1, and the aspect ratio of the peak at 28.0±0.2 to the peak at 28.2±0.1 is 0.9:1 to 1:1,
   the oxidative dehydrogenation catalyst has a 35% conversion temperature of about 355° C. to about 365° C. and a selectivity to ethylene of about 92% to about 99%,
   the oxidative dehydrogenation catalyst has a pore volume from 0.01 cm³/g to 0.10 cm³/g, and
   the oxidative dehydrogenation catalyst has a surface area from 15 m²/g to 65 m²/g, and
   the oxidative dehydrogenation catalyst is prepared by a process comprising wet ball milling a pretreated oxidative dehydrogenation catalyst having the empirical formula:

$$Mo_{1.0}V_{0.12-0.49}Te_{0.05-0.17}Nb_{0.10-0.20}O_d$$

wherein d is a number to satisfy the valence of the oxide.

* * * * *